United States Patent
Van Anholt et al.

(10) Patent No.: US 12,219,979 B2
(45) Date of Patent: Feb. 11, 2025

(54) BOVINE MILK HAVING A HIGH N6-POLYUNSATURATED FATTY ACID CONTENT

(71) Applicant: FrieslandCampina Nederland B.V., Amersfoort (NL)

(72) Inventors: Rogier Daniël Van Anholt, Wageningen (NL); Jeroen Margot Leon Heck, Wageningen (NL)

(73) Assignee: FrieslandCampina Nederland B.V., Amersfoort (NL)

( * ) Notice: Subject to any disclaimer, the term of this patent is extended or adjusted under 35 U.S.C. 154(b) by 663 days.

(21) Appl. No.: 17/437,304

(22) PCT Filed: Mar. 25, 2020

(86) PCT No.: PCT/EP2020/058257
§ 371 (c)(1),
(2) Date: Sep. 8, 2021

(87) PCT Pub. No.: WO2020/193592
PCT Pub. Date: Oct. 1, 2020

(65) Prior Publication Data
US 2022/0175005 A1    Jun. 9, 2022

(30) Foreign Application Priority Data
Mar. 27, 2019   (EP) .................................... 19165477

(51) Int. Cl.
| | | |
|---|---|---|
| A23L 33/12 | (2016.01) | |
| A23C 9/152 | (2006.01) | |
| A23K 20/158 | (2016.01) | |
| A23K 40/35 | (2016.01) | |
| A23K 50/10 | (2016.01) | |
| A23L 33/00 | (2016.01) | |
| A61K 31/201 | (2006.01) | |
| A61K 31/231 | (2006.01) | |

(52) U.S. Cl.
CPC ............ *A23L 33/12* (2016.08); *A23C 9/1528* (2013.01); *A23K 20/158* (2016.05); *A23K 40/35* (2016.05); *A23K 50/10* (2016.05); *A23L 33/40* (2016.08); *A61K 31/201* (2013.01); *A61K 31/231* (2013.01); *A23C 2230/10* (2013.01); *A23V 2002/00* (2013.01)

(58) Field of Classification Search
None
See application file for complete search history.

(56) References Cited

FOREIGN PATENT DOCUMENTS

| | | |
|---|---|---|
| DE | 4327310 | 2/1994 |
| EP | 2329722 | 6/2011 |
| WO | 2001011978 | 2/2001 |
| WO | 2008066380 | 6/2008 |
| WO | 2011008097 | 1/2011 |
| WO | 2011014069 | 2/2011 |
| WO | 2012053893 | 4/2012 |

OTHER PUBLICATIONS

"Enriched Milk Powder"; Mintel; Jan. 2006; http://www.gnpd.com; 2 pages.
Amaral-Phillips, Donna M., et al.; "Should you Be Feeding Fat to Your Dairy Cows?"; Cooperative Extension Service, University of Kentucky, College of Agriculture; ASC-134; 1997; pp. 1-4.
Banas, Antoni, et al.; "Lipids in grain tissues of oat (*Avena sativa*): differences in content, time of deposition, and fatty acid composition"; Journal of Experimental Botany; vol. 58, No. 10; Jun. 22, 2007; pp. 2463-2470.
Bartsch, B. D., et al.; "Production, Composition, and Manufacturing Properties of Milk from Grazing Dairy Cows Fed on a Formaldehyde-treated Sunflower Seed Supplement"; Australian Journal of Agricultural Research; vol. 27, No. 6; Jan. 1, 1976; pp. 917-927.
Clapperton, John L., et al; "The Production of Milk Rich in Protein and Low in Fat, the Fat Having a High Polyunsaturated Fatty Acid Content"; Journal of the Science of Food and Agriculture; vol. 31, No. 12; Dec. 1980; pp. 1295-1302.
Goodridge, J., et al.; "Transfer of omega-3 linolenic acid and linoleic acid to milk fat from flaxseed or Linola protected with formaldehyde 1"; Canadian Journal of Animal Science; vol. 81, No. 4; Dec. 2001; pp. 525-532.
Heguy, J. M., et al.; "Whey protein gel composites of soybean and linseed oils as a dietary method to modify the unsaturated fatty acid composition of milk lipids"; Animal Feed Science and Technology; vol. 131, No. 3-4; Dec. 15, 2006 ; pp. 370-388.
Innis, Sheila M.; "Palmitic Acid in Early Human Development"; Critical Reviews in Food Science and Nutrition; 56:12; 2016; pp. 1952-1959.
Lopez-Lopez, A., et al; "Fatty acid and sn-2 fatty acid composition in human milk from Granada (Spain) and in infant formulas"; European Journal of Clinical Nutrition; 2002; vol. 56, No. 12; pp. 1242-1254.
Luddy, F. E.; et al; "Pancreatic Lipase Hydrolysis of Triglycerides by a Semimicro Technique1"; The Journal of the American Oil Chemists' Society; vol. 41; Oct. 1964; pp. 693-696.
PCT; App. No. PCT/EP2020/058257; International Search Report and Written Opinion mailed Apr. 24, 2020; 18 pages.

(Continued)

*Primary Examiner* — Jyoti Chawla
(74) *Attorney, Agent, or Firm* — Fitch, Even, Tabin & Flannery LLP

(57) ABSTRACT

The present invention relates to bovine milk fat comprising, based on total fatty acid content, 8.9-29.0 wt % linoleic acid (C18:2 cis, 9,12), 0.9-2.4 wt % alpha-linolenic acid (C18:3 cis 9,12,15), and 3-5 wt % butyric acid (C4:0). The present invention further relates to a bovine milk comprising said milk fat and to a method for producing said milk by feeding a lactating bovine mammal with a rumen-protected linoleic acid source and a rumen-protected alpha-linolenic acid source, followed by milking the lactating bovine animal.

13 Claims, No Drawings

(56) References Cited

OTHER PUBLICATIONS

Plowman, R. D., et al; "Milk Fat with Increased Polyunsaturated Fatty Acids"; Journal of Dairy Science; vol. 55, No. 2; Aug. 6, 1971; pp. 204-207.

Walstra, Pieter, et al.; "Dairy Science and Technology": 2006; 2nd Ed.; Taylor & Francis Group, LLC; 16 pages.

Wikipedia; "alpha-Linolenic acid"; Mar. 8, 2019; https://en.wikipedia.org/w/index.php?title=Alpha-Linolenic acid&oldid=886831266, retrieved on Jul. 10, 2019; pp. 1-6.

Wikipedia; "gamma-Linolenic acid"; May 25, 2018; https://en.wikipedia.org/w/index.php?title=Gamma-Linolenic_acid&oldid=842861148; retrieved on Jul. 10, 2019; pp. 1-4.

Wikipedia; "Linoleic acid"; Mar. 21, 2019; https://en.wikipedia.org/w/index.php?title=Linoleic acid&oldid=888801671, retrieved on Jul. 10, 2019; pp. 1-8,.

Wikipedia; "Linolelaidic acid"; Jan. 25, 2018; https://en.wikipedia.org/wiki/Linolelaidic_acid, retrieved on Jul. 10, 2019; pp. 1-2.

Glasser, F., et al.; "Oilseed Lipid Supplements and Fatty Acid Composition of Cow Milk: A Meta-Analysis"; Journal of Dairy Science; 2008; vol. 91, No. 12; pp. 4687-4703.

Lanier, Jennifer Stamey, et al.; "Challenges in enriching milk fat with polyunsaturated fatty acids"; Journal of Animal Science and Biotechnology; 2015; 6:26; pp. 1-9.

BOVINE MILK HAVING A HIGH N6-POLYUNSATURATED FATTY ACID CONTENT

CROSS REFERENCE TO RELATED APPLICATIONS

This application is a U.S. national phase application of International Application No. PCT/EP2020/058257, filed Mar. 25, 2020, which claims benefit from European Patent Application No. 19165477.1, filed Mar. 27, 2019, which are each hereby incorporated herein by reference in their entirety.

FIELD

The invention relates to the field of formula milk, suitable as nutrition for children. In particular, the invention relates to a bovine milk and bovine milk fat that can be used as an ingredient for such formula milk. The invention further relates to a method for producing a bovine milk or a bovine milk fat.

BACKGROUND

Formula milk products, such as infant formulas (for babies under 12 months of age), follow-up formulas (for infants of 6-12 months of age) and growing-up formulas (for toddlers of 12 months and older, typically up to about 3 years of age), are usually produced from (bovine milk) proteins, a fat source, a carbohydrate source, a vitamin-mineral mix, and other ingredients. The fat source is or contains a blend of vegetable oils.

According to requirements set by regulatory bodies and/or recommended by food and health organisations, the fat composition in formula milk products has to contain sufficiently high levels of linoleic acid (C18:2 cis 9,12; herein also referred to as "LA"), and alpha-linolenic acid (C18:3 cis 9,12,15; herein also referred to as "ALA"), and a specific ratio of the two.

Typical LA and ALA contents in regular cow milk fat are, based on total fatty acids, 1-1.5 wt % LA and 0.2-0.8 wt % for ALA. Because these levels are not sufficiently high, bovine milk fat cannot be used as the sole fat source for formula milk products. If bovine milk fat is used, it needs to be formulated in combination with a vegetable oil in order to achieve the required levels of ALA and LA.

Despite the low ALA and LA content of milk fat, milk fat has various advantageous properties compared vegetable fats.

One such advantage relates to its palmitic acid content. Saturated fatty acids, such as palmitic acid (C16:0), are important constituents of a young child's nutrition. Although often considered to have adverse effects on chronic disease in adults, palmitic acid is an essential component of membrane, secretory, and transport lipids, with crucial roles in protein palmitoylation and signal molecules. What is more, there are regulations, directives, and recommendations with respect to palmitic acid content, the soap forming potential, and maximum trans-fatty acid content of formula milk products.

Opposite to milk fat, vegetable oils have a low content of saturated fatty acids such as palmitic acid.

According to S. Innis, *Critical Reviews in Food Science and Nutrition, Volume 56, 2016-Issue 12*, pp 1952-1959, at birth, the term infant is 13-15% body fat. After birth, the infant accumulates adipose tissue at high rates, reaching 25% body weight as fat by 4-5 months age. Over this time, human milk provides 10% dietary energy as palmitic acid, but in unusual triglycerides with palmitic acid on the glycerol centre carbon, i.e. the sn-2 position. Innis also refers to marked deviations in tissues with displacement of palmitic acid that can occur in infants fed vegetable oil formulas. Regular bovine milk contains considerable amounts of palmitic acid, the majority of which is on the sn-1 or sn-3 position. The soap forming potential (i.e. the molar percentage of C12:0+C14:0+C16:0+C18:0 fatty acids on sn-1 or sn-3 position of the glyceride) of regular bovine milk fat is considerably higher than in human milk. The soap forming potential is a measure for the total of calcium soaps that can be formed form the milk fat after digestion by a human, in particular an infant. A high soap forming potential (i.e. a high content of saturated fatty acids, such as palmitic acid, in the sn-1 or sn-3 position), is less favourable with respect to digestion, lipid absorption and stool.

Furthermore, the most prominent vegetable palmitic acid source is palm oil; its harvesting attracts major concerns about the detrimental ecological impact of the large area needed for palm tree plantations to provide palm oil.

A second advantage of milk fat compared to vegetable fat relates to the butyric acid content. Compared to vegetable oils, bovine milk fat contains a relatively large amount of butyric acid, which is known to have a positive effect on immune modulation.

A third advantage of milk fat relates to its beneficial globular structure. The membrane of milk fat globules is a complex and unique structure composed primarily of lipids and proteins that surrounds milk fat globules secreted from the milk producing cells of humans and other mammals. It is a source of multiple bioactive compounds, including phospholipids, glycolipids, glycoproteins, and carbohydrates that have important functional roles within the brain and gut. The globular structure of milk fat is also considered beneficial to digestion. Furthermore, milk fat contains micronutrients, like vitamin D and vitamin E.

DETAILED DESCRIPTION

In view of these positive aspects of milk fat compared to vegetable fat and in order to reduce the number of ingredients needed for formulating formula milk, it would be desirable to be able to use milk fat as the sole fat source or at least to be able to use milk fat as the sole source for LA and/or ALA in formula milk.

This object has been achieved by the present invention. It has been found that by feeding bovine mammals with a specific diet, milk with the desired fat constitution can be obtained. This milk fat comprises, based on the total fatty acid weight, 8.9-29.0 wt % linoleic acid (C18:2 cis, 9,12), 0.9-2.4 wt % alpha-linolenic acid (C18:3 cis 9,12,15), and 3-5 wt % butyric acid (C4:0).

The milk fat obtained from this milk can be used in formula milk and can constitute at least 50 wt %, preferably at least 60 wt %, more preferably at least 70 wt %, even more preferably at least 80 wt %, more preferably at least 90 wt %, and most preferably 100% of the total fat content of the formula milk.

In this specification, the term "milk" includes raw milk, milk that has undergone an anti-microbial treatment (e.g. whole milk or semi-skimmed milk), and concentrated or dried milk.

The term "milk fat" refers relates to the total fat phase of milk, not only to a fraction of it, such as the phospholipid fraction. Milk fat is a complex mixture of triglycerides and other lipid components. Milk fat typically consists for the largest part of triglycerides (e.g. about 98%).

The term "fat" is used herein for triacylglycerides in general (irrespective of the melting point or range) and for lipid compositions substantially consisting of triglycerides in which a minor amount (typically 5 wt. % or less) of one or more other lipid components is present.

The term "fatty acid" encompasses both free fatty acids and fatty acid residues in acyl glycerides, i.e. fatty acid residues bound to glycerol. The content of the different fatty acids in a fat composition can be determined by forming fatty acid methyl esters according to ISO 15884/IDF 182: 2002 (Milk fat—Preparation of fatty acid methyl esters) and subsequently analyzing the methyl esters with gas-liquid chromatography according to ISO 15885/IDF 184 (Milk fat—Determination of the fatty acid composition by gas-liquid chromatography). This allows for the determination of to concentration of specific fatty acids relative to total fatty acid content.

The distribution of fatty acids over the glycerol backbone can be determined according to the method disclosed in Luddy, F. E. et al. *J. Am. Oil Chem. Soc.*, 41, 693-696 (1964). In essence, this method involves hydrolysis of TAG by a sn-1,3 specific pancreatic lipase (porcine). The required 2-monoacylglycerols formed are isolated by thin layer chromatography and these are subsequently methylated for gas chromatographic analysis and quantified in molar concentrations relative to the total moles of fatty acids at the sn-2 position ([FA(sn-2)]). The molar concentration (or mole fraction) of a fatty acid at the sn-1,3 positions of the glycerol backbone relative to total moles of fatty acids in the TAG ([FA(sn-1,3)]) is then calculated from [FA-TAG] and [FA(sn-2)] via the formula: (FA_sn-1,3)=FA_TAG−⅓*FA_sn-2.

It has been known at least since the 1970's that it is possible to increase the content of polyunsaturated fatty acids, like LA, in cow's milk, by feeding cows a vegetable oil encased in a casein particle, see Plowman et al., *Journal of Dairy Science February* 1972, Vol 55, Issue 2, pages 204-207. When using formaldehyde-treated safflower oil-casein particles, the LA content increased from 3% to 35% of total fatty acids. Plowman observed that protection is needed to avoid hydrogenation of polyunsaturated fatty acid (PUFA) in the gastrointestinal tract of the cows. In Goodridge et al., *Canadian Journal of Animal Science* 81 (2001), 552-532, effects of formaldehyde-treated flaxseed and linola in the feed of cows are reported. It was concluded that it would be possible to reduce hydrogenation and thereby increase C18:2 and C18:3 fatty acids in milk fat. However, the fatty acid content given in Table 6 of this document does not add up to 100%. This all sheds doubt on the credibility of the reported fatty acid composition. Furthermore, the butyric acid (C4) content of bovine milk is naturally in the range 3-5 wt %, while that reported in Table 6 is far lower. In addition, this document does not specify which part of the C18:2 fatty acids and C18:3 fatty acid in Table 6 is trans C18:2 respectively C18:3. Only the amount of trans C18:1 was given and it was relatively high.

Despite the long known principle of altering the fatty acid composition of cow's milk by altering the fatty acid composition of the feed to the cows, there have been no reports on the modification of the fatty acid composition of bovine milk in order to provide a favourable composition for use in the production of formula milk for young children.

The main focus has always been on reduction of the total fat content of milk (J. L. Clapperton et al., *J. Sci. Food Agric.* 31 (1980) 1295-1302) or on increasing omega-3 polyunsaturated fatty acids (also known as n3-PUFA's) such as ALA (J. M. Heguy et al., *Animal Feed Science and Technology* 131 (2006) 370-388). For adults, n3-PUFA's have been reported to have health benefits, such as cardio-vascular benefits, whereas high levels of omega-6 PUFA's (also known as n6-PUFA's) such as LA and high levels of saturated fatty acids such as palmitic acid and stearic acid are often considered less healthy, or even to have adverse health effects. The few known publications that refer to milk for infants, focus on increasing n3-PUFA's (e.g. ALA and/or docosahexanoic acid (DHA)) whilst keeping the ratio n6-PUFA's to n3-PUFA's relatively low.

For instance, DE 43 27 310 A1 relates to a milk that is enriched in n3-PUFA's which is said to be important for the mental capabilities and growing-up of humans. This is accomplished by feeding cows a feed comprising 30-60 wt. % n3-PUFA's. The PUFA's are encapsulated using methanol and a reaction product of formaldehyde and casein. The examples show that is was possible to increase ALA to a maximum of 1.8 g/100 g in two weeks). The LA content was not higher than 5.8 g/100 g.

EP 2 329 722 is another publication describing a way to obtain milk with increased levels of unsaturated fats. The disclosed population of cows produced milk fat with less than 60% total saturated fat, less than 10% myristic acid, less than 20% palmitic acid, at least 30% monounsaturated fat (MUFA), at least about 25% C18:1 (total, i.e. including cis and trans), at least 6% PUFA, and at least 5% linoleic acid. The cows were fed a conventional diet. It is stated that the milk may be used for the preparation of various products. e.g. various forms of milk, deserts cheese, butter, chocolate, and infant formula. The butter according to EP 2 329 722 (Table 1, 2) not only shows an increase in LA (from 1.2 to 7.2 wt %) and ALA (from 0.8 to 2.3 wt %), but also an increase in trans C18:1 and a decrease in palmitic acid compared to a control butter.

It is not straight-forward to control the fat composition of milk by the feed given to the mammal producing the milk, because changing the mammal's diet, e.g. by addition of a supplement to its feed, may not only result in an increase in the concentration of certain fatty acids, but may also have a negative impact on the concentration of (other) beneficial fatty acids. For instance, an increase in LA and ALA could be accompanied by an undesirably large increase in the palmitic acid content or an increase in the amount of detrimental fatty acids. See, in this light, also WO 2011/014069 and Glasser et al., *J. Dairy Sc.* 91 (2008), 4687-4703, studying the use of oilseed supplements in cow diets to alter the milk fatty acid (FA) composition and stating that "*Responses were non-significant, linear or quadratic, depending on the FA studied and the supplement*".

Another aspect that should be taken into consideration when producing milk on a commercial scale, is the potentially detrimental effect of increasing fat content of the feed of the mammals. For instance, Amaral-Phillips et al (http://www2.ca.uky.edu/agcomm/pubs/asc/asc134/asc134.pdf) recommends that diets for lactating cows should not exceed 5% total fat from natural fat sources (includes forages, cereal grains, oilseeds, and tallow). Two to three percent would be supplied by the forages and normal cereal grains found in the diet; 2-3% fat could be supplied from oilseeds or tallow, and an additional 2-3% fat (to make a total of 8% fat) can be added by using specialty or ruminally inert fats. Exceeding these recommendations may decrease fibre digestion and cause milk fat depression.

Nonetheless, the present inventors have found that it is possible to provide milk having a fat composition needed for milk formula intended for infants and toddlers, whilst maintaining other conditions in the production of the milk and other features of the milk within an acceptable range.

According to the method of the present invention, a lactating bovine mammal is fed with a rumen-protected LA source and a rumen-protected ALA source, which source may be the same or different, followed by milking the animal. The feed, preferably roughage (e.g. maize or grass), is supplemented with a rumen-protected LA source and rumen-protected ALA source.

Within the context of the present invention, a substance is rumen-protected if less than 50 wt. % of the LA or ALA incorporated in the substance is converted in the area between the mouth and duodenum of the ruminant (see also, EP-A 2 459 001).

In a preferred embodiment, the bovine mammals are selected from the breed of Holstein or Jersey. In particular, good results have been achieved with Holstein Friesian cows. These mammals need not be selected for having a certain advantageous genotype, although a preference exists for mammals having the AA genotype of the gene DGAT1, e.g. as described in WO 2012053893, or a mammal mentioned in EP-A 2 329 722.

The diet involves the feeding of a supplement comprising an LA source and ALA source. The LA source and the ALA source may be the same or different. Instead of including a supplement in the feed, it is also possible to administer the supplement separately from the feed. As an alternative to the use of a supplement or in combination therewith, one may provide a feed having a high content of rumen-protected LA and/or rumen-protected ALA. For instance, one may provide a compound feed or concentrate having a high content of rumen-protected LA and ALA. It is also an option to combine roughage having a high content of ALA with a supplement providing extra LA, or vice versa. For instance, maize silage typically comprises more LA than grass silage. Grass silage typically comprises more ALA than maize silage. Rumen-protected flax can also be used as a feed component to provide a substantial amount of ALA. Furthermore, in case the feed has a sufficiently high content of either LA or ALA, the supplement can be used to provide the other only.

The supplement has a total fat content of at least 50 wt %, preferably 50-95 wt %, more preferably 60-90 wt %, and most preferably 65-85 wt %. based on total weight of the supplement. The supplement preferably comprises at least 4 wt % rumen-protective material, preferably protein. The content of the rumen protective material, in particular protein, preferably is 8-36 wt %, more preferably 12-30 wt %. Optionally further components are present, such as moisture and/or micronutrients (like minerals and/or vitamins). The concentration of said further components in the supplement is typically less than 10 wt %, in particular 1-5 wt %.

The LA content in the supplement is at least 35 g per 100 g fatty acids, preferably 45-90 g per 100 g fatty acids, more preferably 50-75 g per 100 g fatty acids.

The ALA content in the supplement generally is at least 3 g per 100 g fatty acids, preferably 4.5-10 g per 100 g fatty acids, more preferably 5.0-8 g pe r100 g fatty acids.

The lactating mammal is fed a total of at least 100 g, preferably of 200-2000 g, more preferably 200-1500 g, even more preferably 300-1500 g, and most preferably 300-900 g LA per day and at least 10 g, preferably of 20-200 g, more preferably 20-150 g, even more preferably 30-150 g, and most preferably 30-90 g ALA per day. LA and ALA are administered in an effective amount and form whereby at least 25% of the LA and ALA, preferably 50-95%, more preferably 60-90%, and most preferably 65-95% passes the ruminant's duodenum without having been converted into a different fatty acid. In practice, usually at least 50%, preferably 60-95%, more preferably 65-95% of the total daily intake of LA and ALA are administered in a rumen-protected form.

Advantageously, the supplement provides one or more further unsaturated acids, such as conjugated linoleinic acid (CLA) or cis-oleic acid. The total content of unsaturated acids, including LA and ALA, is usually at least 70 g per 100 g fatty acids preferably at least 75 g per 100 g fatty acids, more preferably 80-98 g per 100 g fatty acids, and most preferably 80-90 g per 100 g fatty acids. If present, the CLA content in the supplement is preferably 1.0-10 g per 100 g fatty acid, preferably 2.0-8 g per 100 g fatty acids. If present, the cis oleic acid content in the supplement is preferably 5-25 g per 100 g fatty acid, preferably 10-23 g per 100 g fatty acids.

The supplement may comprise saturated fatty acids, preferably in a content of up to 30 g per 100 g fatty acids, more preferably 5-25 g per 100 g fatty acids, most preferably 10-20 g per 100 g fatty acids. Considering that palmitic acid is a nutritious saturated fatty acid for infants, palmitic acid preferably is the major saturated fatty acid present in the composition (at least 50 wt % of total saturated fatty acid). Particularly good results have been achieved with a supplement having a palmitic acid content in the range of 5-15 g per 100 g fatty acids.

The supplement's content of trans-fatty acids having a non-conjugated carbon-carbon double bond in the trans configuration is preferably 0-3.0 g per 100 g fatty acids, more preferably 2 g per 100 g fatty acids or less, in particular 0.2-1.0 g per 100 g fatty acids. When present, at least a part of the trans-fatty acids having a non-conjugated carbon-carbon double bond in the trans configuration preferably is vaccenic acid (C18:1 trans 11), e.g. in a content of about 0.05 to about 0.3 g per 100 g, or elaidic acid (C18:1 trans 9), e.g. in a content of about 0.05 to about 0.3 g per 100 g. Vaccenic acid and elaidic acid are present in human and bovine milk. Vaccenic acid fatty acid can be concerted by a humans into CLA (C18:2 cis 9 trans 11).

The fatty acids are typically supplied in the form of triglycerides, as fat or oil. Suitable sources of unsaturated fatty acids include seed oils, such as those of linseed, rapeseed, soybeans, walnuts, sunflower, cotton seed, safflower, clary sage seed, *perilla*, chia, and hemp corn oil, and peanut oil, including fractions thereof. Also suitable are marine oils, such as fish oil, algae oil or the like, including fractions thereof. Preferably, the supplement comprises a vegetable oil providing ALA and/or LA, more preferably a vegetable oil selected from the group consisting of soybean oil, linseed oil, rapeseed oil, sunflower oil, fractions of soybean oil, fractions of linseed oil, fractions of rapeseed oil, fractions of sunflower oil, including mixtures comprising one or more of said vegetable oils and/or said fractions. Particularly good results have been achieved with soybean oil.

The supplement can be administered in combination (admixed) with the feed. The feed generally comprises roughage, feed grain and/or compound feed, such as mixed feed. Preferably, the mammal is fed roughage. The roughage can, for example, be maize silage or grass silage, yet other suitable base compositions can equally be used. Grass and maize silage are typical components of a winter diet for Dutch cows.

The feed is preferably rich in fat, which means that the feed comprises more than 4 wt % of fat, typically between 4 and 6 wt % of fat. Higher amounts of unprotected fat or oils can lead to gastric disturbances of a cow.

The content of the supplement fed in combination (admixed) with a feed can be chosen within a wide range, based on common general knowledge and the information disclosed herein. E.g. if the feed consists of roughage, the content will be chosen higher than when the mammal is getting part of its daily feed by grazing. If the feed itself already has a relatively high content of LA or ALA, the amount of needed supplement will also be less. It is not necessary to adjust the daily dosage on the weight of the individual mammal, although one may optimise the results taking into consideration the average daily milk production of individual mammals: if the milk production is relatively high, a relatively high supplementation with LA and ALA may be beneficial.

It has been found possible to modify the fatty acid profile of the milk, in particular to increase LA and ALA content, in the produced milk within 24 hours of starting the administration of rumen-protected fatty acids. Administration of rumen-protected fatty acids can be continued for more than a day, for a about a week or more, for about 8 weeks or more, for about 26 weeks or more, for about a year or more, e.g. until the mammal is no longer lactating. After discontinuation of the administration of rumen-protected fatty acids, the fatty acid profile gradually returns to a similar profile as before starting the administration. This can be a matter of a few days or weeks, Accordingly, when producing milk in accordance with the invention, the lactating mammal is generally fed rumen protected LA and ALA at least once per week, preferably at least once every three days, and typically—on average—every day.

As mentioned above, LA and ALA are typically encapsulated to provide rumen protection, in order to avoid reduction of the LA and ALA and to avoid the formation of trans-esters from it, a process which occurs in the rumen; see Lanier and Corl, *Journal of Animal Science and Biotechnology*, (2015) 6:26.

This ensures that the LA and ALA stay available for the milk that is produced by the mammal. Furthermore, like many other trans-fats having one or more non-conjugated carbon-carbon double bonds in the trans configuration, trans-esters formed from LA or ALA are considered to potentially increase health risks, e.g. the risk of coronary heart disease or systemic inflammation.

One suitable manner of encapsulating fats is disclosed by both Goodridge and Plowman, and involves formaldehyde-treated fatty acid sources. However, the use of formaldehyde is disadvantageous because it is toxic and carcinogenic. Hence, it poses a health hazard during production and for lactating mammal.

A preferred manner of encapsulation is disclosed in WO 2008/066380, WO 2011/008097 and WO2012/053893 and involves encapsulation in a protein. Preferred proteins are milk proteins and vegetable proteins, in particular whey protein, caseins, and soy protein. More preferably, the encapsulation material at least substantially consists of one or more of said preferred proteins. LA and ALA can be encapsulated together or separately. WO 2008/066380 and WO 2011/008097 describe particularly suitable encapsulation methods. Preferably, the feed supplement is prepared by providing an oil-in-water emulsion, of which the oil phase comprises LA and/or ALA, and wherein a stabilising amount of protein is present, followed by denaturing and aggregating the protein, and spray-drying the denatured, aggregated oil-in-water emulsion into dry powder particles.

As will be illustrated by the examples, it has been found possible to obtain milk directly from cows having a fatty acid profile of the milk fat according to the invention, without needing subjecting the milk fat to a fractionation. In particular, the milk fat has a low content of trans-fatty acids with one or more non-conjugated double carbon-carbon bonds: typically 3.0 g per 100 g fatty acids or less, in particular 0.1-2.7 g per 100 g fatty acids, more in particular 0.5-2.5 g per 100 g fatty acids. This allows direct use of the milk fat for infant nutrition, without needing to subject the milk fat to further treatment to reduce the content of undesired trans-fatty acids.

The milk fat can be obtained from the milk by conventional ways.

Although not required for making formula milk, the milk fat may be subjected to fractionation, if so desired for modifying the fatty acid profile. The fractionation may be based on generally known techniques, such as dry fractionation or supercritical fractionation.

The LA content of the milk fat according to the present invention preferably is at least 12 wt %, more preferably at least 13 wt %, and most preferably 14 wt %, based on total fatty acid content. The LA content is preferably not higher 25 wt %, more preferably not higher than 22 wt %, and most preferably not higher than 20 wt %, based on total fatty acid content. The ALA content of the milk fat is preferably is at least 1.0 wt %, more preferably at least 1.1 wt %, most preferably at least 1.2 wt %, based on fatty acid content. The ALA content is preferably not higher than 2.2 wt %, more preferably not higher than 2.0 wt %, and most preferably not higher than 1.8 wt %, based on total fatty acid content.

In particular for use in formula milk, the milk fat according to the invention preferably has a weight to weight ratio linoleic acid to alpha-linolenic acid in the range of 4:1 to 15:1, more preferably in the range of 5:1-10:1.

In addition to ALA and LA, the milk fat according to the invention usually comprises the fatty acids generally present in bovine milk, which are predominantly C4-C18 fatty acids. Higher larger fatty acids (C19-C24) can be present, typically in trace amounts of about 0.2% or less. The contents of other fatty acids than ALA and LA can vary in a wide range, as desired.

As already indicated above, butyric acid provides a health benefit to a young child's nutrition. Besides it contributes to an appreciated flavour, which is positive for feeding compliance. Accordingly, the butyric acid content of the milk fat according to the present invention is in the range of 3-5 wt %, preferably 3-4 g wt %.

Also palmitic acid is an important constituent of a young child's nutrition. Palmitic acid is also one of the major fatty acid components of bovine milk, and may be as high as about 40 wt %, based on total fatty acid content. Despite the increase in LA and ALA, the method according to the present invention allowed to maintain the palmitic acid content of the milk fat at a desired level. This palmitic acid content in the milk fat of the present invention is preferably in the range of 15-40 wt %, more preferably 20-35 wt %, and most preferably 21-30 wt %, based on total fatty acids. At least 30 mol %, preferably 35-55 mol %, most preferably 42-50 mol % of the palmitic acid content is bound to glyceride at the sn-2 position, Preferably, the milk fat contains conjugated linoleic acid (CLA), which is a known healthy fatty acid. Its concentration is preferably in the range of 0.1-2 wt %, more preferably 0.2-1.5 wt %, most preferably 0.4-0.9 wt %, based on total fatty acids.

The milk fat according to the invention preferably has a total saturated fatty acid content, based on total fatty acids of at least 23 wt %, more preferably 35-70 wt %, most preferably 45-75 wt %.

The soap forming potential (defined as the molar percentage of the sum of C12:0+C14:0+C16:0+C18:0 in the sn-1 or sn-3 position (as determined according to Luddy, F. E. et al. *J. Am. Oil Chem. Soc.*, 41, 693-696 (1964)), based on total fatty acids) of the fat fraction in the milk according to the present invention is preferably 55 mol % or less, more preferably in the range of about 30 to 52 mol %, even more preferably in the range of 40-50 mol %, and most preferably in the range 40-45 mol %. This can be achieved without needing to subject the milk or the milk fat obtained from the milk to any further treatment, such as fat fractionation. Herewith, bovine milk (fat) that has a soap forming potential relatively close to that of human milk (According to Lopez-Lopez et al, *Eur J Clin Nutr.* 56(12) (2002), 1242-54, the soap forming potential of human milk is around 30 mol %) can be directly obtained.

The mono-unsaturated fatty acid content of the milk fat according to the invention, based on total fatty acids, is preferably in the range of 15-30 wt %, more preferably of 22-28 wt %, most preferably 23-27 wt %.

The poly-unsaturated fatty acid content of the milk fat according to the invention, based on total fatty acids of the milk fat, is preferably in the range of 10.0-30 wt %, preferably 11.0-20 wt %, more preferably 12.0-15 wt %.

Further, stearic acid (C18:0) can be present in the milk fat in a content of 5-20 wt %, more preferably 8-18 wt %, based on total fatty acids.

Also oleic acid (C18:1 cis) can be present in the milk fat, the content preferably being in the range of 10-40 wt %, more preferably 15-35 wt %, most preferably 18-25 wt %, based on total fatty acids.

It is a further an important advantage of the invention that it provides a fat suitable for use in the production of, e.g., infant formulae, wherein at least a substantial part of the fat is native globular milk fat. Such native membranes comprise phospholipids and membrane proteins as originally present in the milk fat globules. Preferably, 50-100 wt %, more preferably 75-100 wt %, in particular 90-100 wt. % of the milk fat is globular milk fat, comprising the milk fat globule membrane. The globular milk fat content can be determined as described in Walstra et al, *Dairy Science and Technology*, $2^{nd}$ edition, 2006, CRC Press, in particular chapter 3.2. Hence, the invention not only provides a means to provide fat with sufficient LA and ALA to meet European infant food regulations, but also provides a source of nutritious bioactive lipids and vitamins. Furthermore, the provision of fatty acids in the form of globular fat is advantageous from a digestibility perspective. The invention thereby provides a natural way of providing fat in globular form suitable for the formulation of infant nutrition.

Conventional cow milk generally contains at most a trace of Docosahexaenoic acid (DHA; 22:5n-3), an important fatty acid for the cognitive and visual development, as well as the immune system of young children. In principle, it is possible to increase DHA content in bovine milk, by feeding a DHA-containing supplement to the lactating cow or to add DHA to milk fat according to the invention. However, it may be preferred to add DHA in a desired amount when formulating a food product according to the invention. Suitable amounts can be based on general recommendations for the specific food product. For an infant formula, DHA is preferably provided in a concentration as recommended by health institutes, e.g. in an amount of at least 0.1 g DHA per 100 g fatty acids, in particular of 0.3-0.5 g/100 g fatty acids. The DHA can be obtained from any food-grade source, such as oil from an aquatic animal, like a fish oil, or oil from algae. Likewise, it is possible to add one or more other fatty acids, in line with recommendation by health institutes, e.g. arachidonic acid.

In a further aspect, the present invention is directed to a milk fat, respectively a milk fat from a ruminant other than bovines, in particular a ruminant selected from the group consisting of goats and sheep, the milk fat respectively milk fat composition comprising 8.9-29.0 g/100 g LA and 0.9-2.4 g/100 g ALA based on total fatty acids. The milk fat respectively milk fat composition can be obtained by feeding a lactating ruminant with a rumen-protected linoleic acid source and a rumen-protected alpha-linolenic acid source.

The milk fat or milk according to the invention is in particular suitable for use as an ingredient in the production of a food product, in particular formula milk. The formula milk usually is selected from the group of infant formulas, follow-up formulas and growing-up formulas. Accordingly, the invention further relates to a food product, typically a food product for a child, such as formula milk, in particular an infant formula, a follow-up formula or a growing-up formula, comprising a fat phase, wherein the fat phase comprises bovine milk fat according to the invention. Typically, the fat phase consists for at least 50 wt. %, more preferably at least 60 wt %, more preferably at least 70 wt %, even more preferably at least 80 wt %, more preferably at least 90 wt %, even more preferably at least 95 wt %, and most 100 wt % of said milk fat.

EXAMPLES

Materials and Methods

Feed Supplement Preparation (Rumen Protected)

A vegetable oil (soybean) having a fatty acid composition as shown in Table 1 was encapsulated with whey protein (WPC 80) in a weight ratio of about 78 soybean oil to 17 whey protein, using the following method:

1000 kg of an emulsion was prepared by mixing 663 kg water, 272 kg of soybean oil, and 66 kg WPC 80 (extrion PROGEL, FrieslandCampina; 80% protein in dry matter) in a stirred vessel, under homogenization using a Ultra Turrax®, temperature 60° C. Then the emulsion was homogenized again in a high pressure homogenizer at a pressure of 350/50 bar at 60° C., followed by a heat treatment at 82° C. for 1 hour. The heated emulsion was cooled to 55° C. and spray dried using a Spraying Systems nozzle configuration 64/21 at a pressure of 70 bar. Inlet temperature was 155° C., outlet temperature 68° C. The powder contained 79.6 wt % fat, 17.1 wt % protein, 1.2 wt % moisture. The fatty acid composition is shown in Table 1.

TABLE 1

| Fatty acid composition | Fatty acid (wt % fat) |
| --- | --- |
| C14:0 myristic acid | 0.2 |
| C16:0 palmitic acid | 10.8 |
| C18:0 stearic acid | 1.5 |
| C18: 1cis oleic acid | 22.6 |
| C18:2cis linoleic acid | 58.9 |
| C18:3-9cis alpha-linolenic acid | 5.3 |
| C18:3-6cis gamma-linoleic acid | 0.3 |
| C20:1 gadoleic acid | 0.4 |
| C20:3 eicosatrienoic acid | 0.6 |
| C20:5 eicosapentaenoic acid | 0.5 |
| Trans fatty acids | 0.7 |

Cows

Twelve lactating Holstein Friesian cows (age >85 days) were selected and grouped according to their average milk fat content of the preceding milk controls. They were then randomly assigned to one or two treatment groups (group 1 or group 2). The main characteristics are shown in Table 2.

TABLE 2

|  | Group 1 | Group 2 |
|---|---|---|
| Lactation (days) | 104 ± 30 | 131 ± 30 |
| Lactation (times) | 3.8 ± 0.5 | 3.8 ± 0.5 |
| Milk (L/day) | 29.8 ± 2.1 | 31.5 ± 1.7 |
| Fat (g/100 mL) | 4.14 ± 0.2 | 4.07 ± 0.32 |
| Protein (g/100 mL) | 3.48 ± 0.19 | 3.41 ± 0.18 |
| Lactose (g/100 mL) | 4.33 ± 0.06 | 4.39 ± 0.08 |
| Urea (mg/100 mL) | 21.8 ± 1.8 | 24.5 ± 2.0 |

Feeding Regime

The cows were fed either only standardized feed or standardized feed supplemented with either a low dosage of the rumen-protected supplement (0.8 kg supplement/cow/day) or a high dosage of the rumen-protected supplement (1.6 kg supplement/cow/day). More specifically, the standardized feed consisted of grass silage 11-12 kg/cow/day, based on dry matter, and concentrate 8-9 kg/cow/day, based on dry matter. For the cows receiving the supplement, concentrate was iso-energetically replaced by the supplement The feeding regime for each of the groups was as shown in Table 3.

TABLE 3

|  | Period 1 (weeks 1-2)* | Period 2 (weeks 3 + 4) | Period 3 (weeks 5 + 6) | Period 4 (weeks 7 + 8) |
|---|---|---|---|---|
| Group 1 | Standardized feed | Low dose supplement | High dose supplement | Standardized feed |
| Group 2 | Standardized feed | High dose supplement | Low dose supplement | Standardized feed |

Results

The cows were milked twice a day throughout the test period. Table 4 shows the results fat composition of the milk samples collected at the end of a period of two weeks of standardized feeding, low dosage LA&ALA rumen protected feeding and high dosage LA&ALA rumen protected feeding. The data were obtained by gas chromatography and data were averaged to provide mean values for the period of low feeding, respectively high feeding, wherein the results of groups 1 and 2 have been combined. The fraction of fatty acid at sn-2 or at sn-1/sn-3 was determined as described by Luddy, et al. (see above). The protein content was determined using a routine infrared red analyser (FTIR) mid infrared with A FOSS instrument (Milcoscan).

TABLE 4

| Fatty acid (g/100 FA) | before feeding (n = 8 cows) | low feeding (n = 8 cows) | high feeding (n = 8 cows) | after feeding (n = 8 cows) |
|---|---|---|---|---|
| C4:0 | 3.56 | 3.85 | 4.04 | 3.86 |
| C6:0 | 2.37 | 2.52 | 2.44 | 2.51 |
| C8:0 | 1.33 | 1.39 | 1.28 | 1.37 |
| C10:0 | 3.06 | 2.93 | 2.58 | 3.05 |
| C12:0 | 3.63 | 3.22 | 2.78 | 3.59 |
| C14:0 | 12.43 | 10.18 | 9.00 | 12.31 |
| C16:0 | 34.77 | 24.97 | 22.05 | 37.22 |
| C18:0 | 8.67 | 12.16 | 13.22 | 8.03 |
| C18:1 cis 9 | 15.46 | 18.73 | 20.3 | 14.45 |
| C18:2 cis 9, 12 | 1.42 | 8.02 | 10.83 | 1.28 |
| C18:3 cis 9, 12, 15 | 0.69 | 1.34 | 1.55 | 0.47 |
| CLA: C18:2 cis 9 trans 11 | 0.39 | 0.43 | 0.41 | 0.33 |
| Saturated | 74.12 | 64.73 | 60.25 | 76.01 |
| Mono unsaturated | 21.42 | 23.74 | 25.18 | 20.12 |
| Poly unsaturated | 2.86 | 10.12 | 13.34 | 2.4 |
| Trans FA*** | 1.37 | 1.53 | 1.58 | 1.17 |
| Soap forming potential (Mol %)* | 58.48 | 47.97 | 46.4 | 58.72 |
| C16:0 @ sn-2** | 40.96 | 43.92 | 42.06 | 42.1 |
| Milk composition |  |  |  |  |
| Fat % | 4.18 | 4.41 | 4.59 | 4.35 |
| Protein % | 3.50 | 3.46 | 3.42 | 3.44 |
| Fat/Protein (ratio) | 1.2 | 1.3 | 1.3 | 1.3 |

*Soap forming potential = Sum of the molar proportions of C12:0, C14:0, C16:0 and 18:0 at the sn-⅓ position = C12:0 (sn 1, 3) + C14:0 (sn 1, 3) + C16:0 (sn 1, 3) + C18:0 (sn 1, 3)
**C16:0@ sn-2 = (C16:0(sn-2)/(3*C16:0(TAG))*100, i.e. % of total C16:0 that is esterified at sn-2 position
***comprising a non-conjugated trans C = C The results in Table 4 illustrate that it is possible to obtain milk having milk fat wherein the content of both LA and ALA is within the range of 8.9-29.0 g/100 g LA, based on total fatty acids; and 0.9-2.4 g/100 g ALA, based on total fatty acids, without needing to subject the milk fat to any treatment. This was found possible whilst at least maintaining desired saturated fatty acid at a desired level: the butyric acid is maintained at essentially the same level, palmitic acid is reduced yet maintained above 20 g/100 g. Further, soap forming potential is reduced to a preferred level. Further, the table shows beneficial results for unsaturated fatty acids, like oleic acid (C18:1 cis) and CLA, for which the levels are increased or maintained.

The invention claimed is:
1. Bovine milk fat comprising, based on a total fatty acid weight;

a. 8.9-29.0 wt % linoleic acid (C18:2 cis, 9,12),
b. 0.9-2.4 wt % alpha-linolenic acid (C18:3 cis 9,12,15), and
c. 3-5 wt % butyric acid (C4:0),
wherein a weight ratio of linoleic acid to alpha-linolenic acid is in a range of 4:1-10:1.

2. Bovine milk fat according to claim 1, wherein the weight ratio of linoleic acid to alpha-linolenic acid is in a range of 5:1-10:1.

3. Bovine milk fat according to claim 1, comprising 11-20 wt % linoleic acid, and preferably 12-18 wt % linoleic acid, based on total fatty acids.

4. Bovine milk fat according to claim 1, comprising 15-40 wt % palmitic acid (C16:0).

5. Bovine milk fat according to claim 4, wherein at least 30% of the palmitic acid is bound to glyceride at the sn-2 position.

6. Bovine milk fat according to claim 1, comprising 8-18 wt % stearic acid (C18:0).

7. Bovine milk fat according to claim 1, having an oleic acid content (C18:1 cis) in the range of 15-35 wt %.

8. Bovine milk fat according to claim 1, wherein the fat comprises at most 3.0 wt %, preferably 0.5-3.0 wt %, and most preferably 0.5-2.5 wt % fatty acids with one or more non-conjugated carbon-carbon double bonds in the trans position.

9. Bovine milk fat according to claim 1, having a soap forming potential defined as the molar percentage of the sum of C12:0, C14:0, C16:0, and C18:0 in the sn-1 or sn-3 position, based on total fatty acids of 55 mol % or less, preferably in the range of 30-52 mol %, in particular in the range of 40-50 mol %.

10. Bovine milk wherein the fat phase consists of the bovine milk fat according to claim 1.

11. Bovine milk according to claim 10 wherein at least 50 wt %, preferably 90-100 wt. % of the bovine milk fat is globular milk fat.

12. Formula milk comprising a fat phase, wherein the fat phase consists of at least 50 wt. %, preferably at least 60 wt %, more preferably at least 70 wt %, even more preferably at least 90 wt %, and most preferably 100 wt % of the bovine milk fat according to claim 1.

13. The formula milk of claim 12, wherein the formula milk is an infant formula, a follow-up formula, or a growing-up formula.

\* \* \* \* \*